United States Patent [19]

Milionis et al.

[11] 4,432,787

[45] Feb. 21, 1984

[54] CONCENTRATED EMETIC HERBICIDAL COMPOSITION AND METHOD FOR THE PREPARATION THEREOF

[75] Inventors: Jerry P. Milionis, Somerset; Joel E. Fischer, Hightstown, both of N.J.

[73] Assignee: American Cyanamid Company, Stamford, Conn.

[21] Appl. No.: 360,545

[22] Filed: Mar. 22, 1982

[51] Int. Cl.³ ............................................. A01N 25/32
[52] U.S. Cl. ................................... 71/94; 71/DIG. I; 424/10
[58] Field of Search ................ 71/94, DIG. I; 424/10

[56] References Cited

U.S. PATENT DOCUMENTS

| | | | |
|---|---|---|---|
| 3,920,443 | 11/1975 | Drewe et al. | 71/94 |
| 4,046,558 | 9/1977 | Davies et al. | 424/10 |
| 4,075,005 | 2/1978 | Knowles et al. | 71/94 |
| 4,160,017 | 7/1979 | Davies et al. | 424/10 |

FOREIGN PATENT DOCUMENTS 56-61301 5/1981 Japan.
WO80/0023 11/1980 PCT Int'l Appl. .

*Primary Examiner*—Catherine L. Mills
*Attorney, Agent, or Firm*—Thomas J. Monahan; H. G. Jackson

[57] ABSTRACT

A concentrated emetic herbicidal composition comprising an aqueous salt of a herbicidal bipyridinium quaternary cation, a nonionic surfactant, a peripherally-acting emetic, and a malodorous synergist for said peripherally-acting emetic. A method for rendering herbicidal compositions emetic to warm-blooded animals is also described.

6 Claims, 1 Drawing Figure

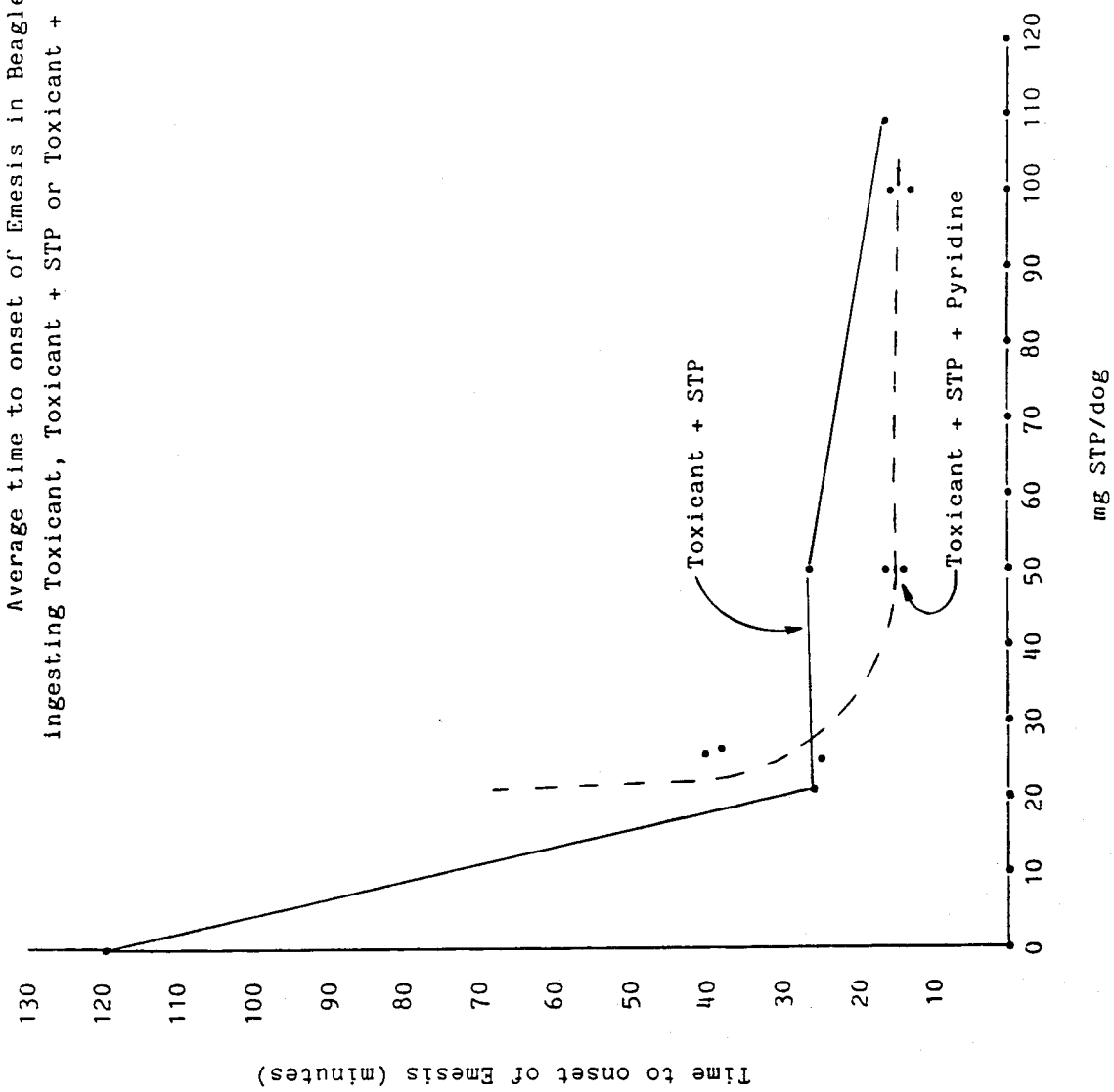

CONCENTRATED EMETIC HERBICIDAL COMPOSITION AND METHOD FOR THE PREPARATION THEREOF

The invention herein described relates to a concentrated herbicidal composition containing a bipyridinium quaternary cation. This compound is notably toxic to warm-blooded animals. The composition of the invention promptly induces emesis thereby disgorging the ingested composition.

By way of background, the bipyridinium quaternary cation utilized in the composition of the present invention is disclosed as a highly effective herbicidal agent useful for the control of undesirable vegetation in U.K. Pat. No. 813,531 (1959). This herbicidal agent is commonly referred to as paraquat.

This compound rapidly destroys green plant tissue primarily by a contact mechanism but with some translocation. Since paraquat is a fast-acting, highly-effective herbicidal agent and is rapidly inactivated when in contact with soil, this compound has been accepted by the agricultural industry and used extensively throughout the world for a variety of weed control problems including: control of undesirable weeds in plantation crops, inter-row weed control in vegetable crops, and clearing of weeds from pasture lands.

In spite of the fact that paraquat and paraquat salts have been used extensively for agricultural purposes throughout the world over the past two decades, these materials remain dangerous to handle, store, or utilize. This danger exists even though precautionary practices and procedures are prescribed by governmental agencies and agricultural institutions. Unfortunately, some operators dealing with paraquat do not always follow safety procedures. It is not uncommon to find improper handling, storage or use of the product which results in either accidental or intentional ingestion by animals or humans. Death is a common result of any such ingestion of paraquat.

By way of further background, the following patents and other publication may be used to supplement this specification: Weaver, J. E. and Griffith, J. F. 1966. Induction of emesis by detergent ingredients and formulations. Toxicol. & Appl. Pharmacol., 8:362 (abstract); Weaver, J. E. and Griffith, J. F. 1969. Induction of emesis by detergent ingredients and formulations. Toxicol. & Appl. Pharmacol., 14:214-220; Japanese Pat. No. 61,301 (1981); U.K. Pat. Nos. 813,531 (1959), 1,406,881 (1975), 1,506,568 (1978), 1,507,407 (1978); and U.S. Pat. Nos. 4,046,552 (1977), 4,118,218 (1978), 4,160,017 (1979), and 4,269,820 (1981).

Paraquat is generally sold commercially as a 20% aqueous solution of the cation. The toxic dose for man has been estimated at 10–15 ml, equivalent to 2400 mg, or 40 mg/kg (60 kg basis). (Murphy, S., 1980, In Casarett and Doull's Toxicology, Second Ed., Macmillan Publishing Co., Inc., New York, pp. 390–392.) Up to 20% of the administered dose is absorbed through the mucosa of the stomach and intestines, reaches a maximum blood concentration within about two hours following ingestion, and is then rapidly excreted in the urine. Excretion usually occurs within 48 hours. However, hypersusceptability of the lung to paraquat leads to lung impairment and delayed death, particularly if blood levels exceed 0.2 mg/ml of plasma (Davies, 1977). Treatment has generally been limited to early removal from the stomach by emetics and/or cathartics, and binding the paraquat on clay, (i.e., fuller's earth) to prevent absorption. It has been suggested that the addition of an effective emetic to paraquat formulations may aid in preventing absorption and thereby prevent death following ingestion of the herbicide. It has also been suggested that the addition of a stench to paraquat and other pesticide compositions may discourage inadvertent animal or human ingestion of paraquat formulations.

Studies have shown that emesis is a reflex act stimulated by afferent neurologic pathways from receptors in the pharynx, stomach, duodenum, heart, kidney, bladder, brain, and semicircular canals to the vomiting center in the medulla, which triggers efferent pathways to the involved muscles of the diaphragm, abdomen, thoracic cage, and the pharyngeal region. The reflex is similar in man, dog, swine, and cat, but it is absent in most rodents.

Emetics may act peripherally by activating receptors in the gastric mucosa, which stimulate the vomiting center, or they may act centrally by stimulating an "emetic chemoreceptor trigger zone" which then stimulates the vomiting center. Examples of emetics acting peripherally are sodium tripolyphosphate and tetrapotassium pyrophosphate. Arecotine and apomorphine are typical central-acting emetics, as demonstrated by a blocking of the emetic action by chlorpromazine (Weaver and Griffith, 1969). Copper sulfate is an example of a emetic having both a peripheral and a central mode of action.

Peripheral activity is an important characteristic of an effective emetic since rapid action is necessary and effective dosages are independent of body weight. Thus, a potential emetic need only exceed the threshold dose to trigger the gastric mucosal receptors.

A substantial number of chemical compounds and compositions are known to induce emesis in animals and humans. The mode of action of different emetic agents is known to vary with their respective chemical compositions. As noted above, some emetic agents act upon the chemoreceptor trigger zone in the medulla while other agents affect the receptors in the mucosa of the gastrointestinal tract. Still other agents act upon both trigger zones.

To be effective in reducing the health hazards associated with toxic pesticidal compositions, the emetic included in these compositions must be compatible with all of the chemical components of the composition, including the toxicant, surfactant (i.e., wetting agent, detergent, dispersant, or emulsifier), defoamer, pH adjusting agent, or the like. It should not adversely affect the biological activity or physical characteristics of the composition to which it is added, nor should it be inactivated by the chemical composition to which it is added. Given these limitations, the finding of a compatible emetic for a given pesticide composition can be a rather complicated and difficult undertaking.

The finding of a compatible emetic for certain pesticidal agents, (i.e., herbicidal bipyridinium quaternary salts), appears to be further complicated by the finding that some emetic agents, expecially those that act centrally by stimulating an emetic chemoreceptor trigger zone, cause excessive vomiting. With some animals, it has been found that ingestion of a bipyridinium quaternary salt composition containing a centerally-acting emetic causes repeated emesis over a period of from one to two hours. It has also been found that some of these animals disgorge not only the toxicant solution, but also bile from the stomach and even fecal matter from the intestinal tract. Excessive vomiting by an animal, to the extent mentioned above, is not, of course, desirable since it has a deleterious effect on the animals overall body condition and impairs and/or delays detoxification of the animal.

In light of the foregoing summary of some demands and limitations of conventional paraquat formulations, an object of this invention is to provide an improved emetic herbicidal composition containing a salt of a herbicidal bipyridinium quaternary cation, which following ingestion by humans or animals promptly induces emesis for a limited period of time sufficient to disgorge the ingested toxicant composition.

A further object of this invention is to provide a concentrated herbicidal composition comprising an aqueous solution of a salt of a herbicidal bipyridinium quaternary cation, a surfactant, a synergist for a peripherally-acting emetic, and an emetically-effective amount of a peripherally-acting emetic which activates for a limited time period the receptors in the gastric mucosa of the human or animal that ingests the herbicidal composition.

In accordance with the objectives of this invention, there is provided a concentrated emetic herbicidal composition of reduced health hazard comprising an aqueous salt of a herbicidal bipyridinium quaternary cation having the structural formula:

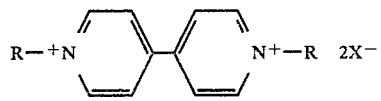

wherein R is a $C_1$–$C_4$ alkyl radical and X is an anion; a nonionic surfactant; an emetically-effective amount of a synergist for the peripherally-acting emetic.

In the compounds illustrated above, R and $R_1$ may be the same or different and may be selected from methyl, ethyl, n-propyl, i-propyl, n-butyl, i-butyl, sec-butyl, or t-butyl; X may be an anion selected from chlorine, bromine, sulfate, methyl sulfate, phosphate, acetate, benzoate, p-toluenesulfonate and propionate.

The preferred compound for use in the compositions of this invention is 1,1'-dimethyl-4,4'-bipyridinium dichloride. The compound 1,1'-ethylene-2,2'-bipyridylium dibromide may be substituted for 1,1'-dimethyl-4,4'-bipyridinium dichloride in the compositions of the invention with similar reduction in the health hazards of herbicidal compositions thereof.

Among the nonionic surfactants which may be employed in the compositions of this invention are: polyoxyethylene ethers of octyl and nonylphenols, polyethylene glycol dioleates; polyoxyalkylene laurates; polyoxyethylene ether of fatty alcohols, polyoxyethylene sorbitan monolaurate and other similar compounds.

Among the peripherally-acting emetics useful in the present invention are: sodium tripolyphosphate and tetrapotassium pyrophosphate. Sodium tripolyphosphate is preferred.

The synergist for the emetic is pyridine.

The aqueous emetic herbicidal concentrates of the present invention contain water; about 100 to 250 mg/ml (preferably 200 to 250 mg/ml) of the bipyridinium quaternary cation; about 10 to 20 mg/ml (preferably 10 to 15 mg/ml) of the peripherally-acting emetic; about 45 to 67.5 mg/ml of the nonionic surfactant; and about 5 to 10 mg/ml (preferably about 5 mg/ml) of pyridine. If desired, a defoaming agent such as silicone can also be included in the composition in an amount equivalent to about 0.5 to 0.75 mg/ml (preferably about 0.5 mg/ml).

It has been discovered that compositions of the invention promptly induce emesis in warm-blooded animals following ingestion. Moreover, we have surprisingly found that ingestion of the compositions by a warm-blooded animal, in an amount sufficient to provide the animal with about 6 to 13 mg of the peripherally-acting emetic and about 3 to 4 mg of pyridine per kg of animal body weight, reduces the time to onset of emesis in the animal about 44% when contrasted to animals ingesting a similar composition which provides each animal with only about 3 to 4 mg per kg of the peripherally-acting emetic and about 1 to 2 mg per kg of body weight.

Surprisingly, we have found that with the compositions of the invention, animals ingesting these compositions vomit only about one or two times in the first 15 minutes following ingestion; whereas, animals ingesting the same herbicide in a composition containing a centerally-acting emetic show repeated vomiting, i.e., up to ten times in the first two hours following ingestion. In some instances, these latter animals bring up bile from the stomach and fecal matter from the intestinal tract.

The following non-limiting Examples further serve to illustrate the invention.

EXAMPLE 1

Determination of the Emetic $Dose_{99}(ED_{99})$ in beagle dogs dosed with 5 ml of a 1.0%, 3.0%, 5.0% or 7.5% solution of sodium tripolyphosphate The following tests were conducted in order to determine the Emetic $Dose_{99}(ED_{99})$ of sodium tripolyphosphate in beagle dogs.

In the tests, ten male and ten female purebred beagle dogs were selected and individually housed in stainless steel cages. The dogs were acclimated to laboratory conditions for at least two weeks prior to testing. The dogs were housed in a heated and air conditioned room at 68° to 74° F. with a relative humidity of 40 to 60%. The lighting was provided by fluorescent fixtures on a 12-hour light-dark cycle. The dogs were provided with 300 g/day of a standard commercial dog chow, and water was provided ad libitum by an automatic watering system. At the end of the two-week acclimation period, the dogs were randomly selected and divided into four treatment groups. Each group was made up of two males and two females. The dogs were 18 to 24 months of age and had a weight range of 7.7 to 14.0 kg for males and 7.1 to 10.5 kg for females.

For these tests, 1.0%, 3.0%, 5.0% and 7.5% sodium tripolyphosphate test solutions were prepared by dissolving appropriate amounts of sodium tripolyphosphate (W/V) in tap water.

All dogs in group A received 5 ml of the 1.0% STP (sodium tripolyphosphate) solution. Dogs in group B received 5 ml of the 3.0% STP solution; dogs in group C received 5 ml of the 5% STP solution, and those in group D received 5 ml of the 7.5% STP solution.

The dogs were dosed by means of a syringe and metal canula. The test solutions were placed at the base of the tongue so that the dogs could swallow the test solutions.

Each animal was weighed prior to dosing to determine the dose given on a mg per kg of animal weight basis. The following observations were made: time of dosing, symptoms of nausea, time of onset of emesis, duration of emesis, number of times vomiting, and the number of dogs vomiting. General signs of abnormal behavior and signs of gross intoxication were also recorded.

The total number of emetic responses at each dose level was recorded and subjected to probit analysis to determine the Emetic Dose$_{99}$(ED$_{99}$).

TABLE I

Determination of the Emetic Dose$_{99}$ (ED$_{99}$) of Sodium Tripolyphosphate in Beagle Dogs
Summary of Experimental Results

| Group | Body Wt. (kg) | Dose (mg/kg) | Symptoms of Nausea | Onset of Emesis (Minutes) | No. of Times Vomiting |
|---|---|---|---|---|---|
| DOSE LEVEL: 5 ML/DOG OF A 1.0% SOLUTION | | | | | |
| A | 11.0 | 4.55 | LL | NE | — |
| A | 12.2 | 4.10 | LL | NE | — |
| A | 7.3 | 6.85 | LL,C,UR | NE | — |
| A | 10.5 | 4.76 | — | NE | — |
| DOSE LEVEL: 5 ML/DOG OF A 3.0% SOLUTION | | | | | |
| B | 14.0 | 10.71 | S | NE | — |
| B | 7.7 | 19.48 | LL | NE | — |
| B | 7.1 | 21.13 | LL | NE | — |
| B | 9.3 | 16.13 | — | 1 | 1 |
| DOSE LEVEL: 5 ML/DOG OF A 5.0% SOLUTION | | | | | |
| C | 10.9 | 22.94 | — | <1 | 2 |
| C | 10.2 | 24.51 | — | 2 | 2 |
| C | 7.9 | 31.65 | LL | NE | — |
| C | 8.7 | 28.74 | LL | NE | — |
| DOSE LEVEL: 5 ML/DOG OF A 7.5% SOLUTION | | | | | |
| D | 11.5 | 32.61 | — | 1 | 1 |
| D | 7.8 | 48.08 | — | 1 | 1 |
| D | 9.8 | 38.27 | — | <1 | 2 |
| D | 8.4 | 44.64 | G | 1 | 1 |

SUMMARY:

| DOSE OF SODIUM TRIPOLYPHOSPHATE (% SOL.) | | | | |
|---|---|---|---|---|
| | 1.0 | 3.0 | 5.0 | 7.5 |
| NO. VOMITING/NO. DOSED | 0/4 | 1/4 | 2/4 | 4/4 |

ED$_{99}$
8.12% SOLUTION

LL = LIP LICKING
G = GAGGING
C = COUGHING
S = SALIVATING
UR = URINATING
NE = NO EMESIS

From these data, it can be seen that emesis was observed in 0/4 dogs at the 1.0% level, 1/4 dogs at the 3.0% level, 2/4 dogs at the 5.0% level, and 4/4 dogs at the 7.5% level. Emesis occurred from <1 to 2 minutes after dosing. Signs of nausea consisted of lip licking, coughing, and gagging prior to emesis.

EXAMPLE 2

Determination of emesis in beagle dogs dosed with 5 ml of a 20.05% aqueous solution of 1,1'-dimethyl-4,4'-bipyridinium dichloride containing 1% of sodium tripolyphosphate and 0.5% pyridine In these tests, ten beagle dogs, (five male, 5 female) eight to 16 months of age and weighing 6.8 to 9.2 kg for males and 5.8 to 8.0 kg for females, were acclimated to laboratory conditions, as described in Example 1, for at least two weeks prior to testing.

The test procedures employed, including: animal feed, drinking water, housing conditions, dosing technique and observation criteria, were the same as described in Example 1 above, excepting that 5 ml of the test solution described below was administered to the test animals.

Data obtained are reported in Table II below.

| Test Solution | |
|---|---|
| Ingredient | % W/V |
| 1,1'-Dimethyl-4,4'-bipyridinium dichloride* | 20.05 (cation) |
| Nonylphenol condensed with 20 moles of ethylene oxide | 6.75 |
| Pyridine (stench) | 0.50 |
| Silicone defoamer | 0.05 |
| Sodium tripolyphosphate | 1.00 |
| Water, qs to 100% | |

*40% technical aqueous solution assayed 42.58% dichloride (w/w)

Five ml of the above solution provides each animal with 50 mg STP, 25 mg pyridine, 2.5 mg silicone defoamer, 1002.5 mg (cation) of the toxicant 1,1'dimethyl-4,4'-bipyridinium dichloride and 337.5 mg of the surfactant nonylphenol condensed with 20 moles of ethylene oxide.

TABLE II

Determination of emesis in beagle dogs dosed with 5 ml of an aqueous 20.05% solution of 1,1'-dimethyl-4,4'-bipyridinium dichloride containing 1% of sodium tripolyphosphate and 0.5% pyridine.
Summary of Experimental Results

| Dog No. and Sex | Body Wt. (kg) | Dose Solution ml/dog | Dose Toxicant mg/kg* | Onset of Emesis (minutes) |
|---|---|---|---|---|
| 1-M | 9.2 | 5 | 108.9 | 8.3 |
| 2-M | 6.8 | 5 | 147.4 | 11.4 |
| 3-M | 7.8 | 5 | 128.5 | 21.5 |
| 4-M | 7.6 | 5 | 131.8 | 22.4 |
| 5-M | 6.8 | 5 | 147.4 | 12.4 |
| 6-F | 7.8 | 5 | 128.5 | 13.1 |
| 7-F | 8.0 | 5 | 125.3 | 19.4 |
| 8-F | 7.8 | 5 | 128.5 | 14.1 |
| 9-F | 7.7 | 5 | 130.1 | 5.5 |
| 10-F | 5.8 | 5 | 172.8 | 13.7 |
| Average | 7.5 | | 134.9 | 14.2 |

*1,1'-Dimethyl-4,4'-bipyridinium cation mg/kg of animal body weight.

From the above date, it can be seen that emesis occurred in all dogs an average of 14.2 minutes after dosing.

EXAMPLE 3

Determination of emesis in beagle dogs dosed with 5 ml of a 21.49% aqueous solution of 1,1'-dimethyl-4,4'-bipyridinium dichloride containing 1% of sodium tripolyphosphate and 0.5% pyridine The procedure of Example 2 was repeated using four beagle dogs eight to 16 months of age and weighing 8.0 to 10.8 kg for males and 8.5 to 8.6 kg for females.

The toxicant formulation administered to the animals had the following composition:

| Test Solution | |
|---|---|
| Ingredient | % W/V |
| 1,1'-Dimethyl-4,4'-bipyridinium dichloride* | 21.49 (cation) |
| Nonylphenol condensed with 20 moles of ethylene oxide | 6.75 |
| Pyridine (stench) | 0.50 |
| Silicone defoamer | 0.05 |
| Sodium tripolyphosphate | 1.00 |
| Water, qs to 100% | |

*40% technical aqueous solution assayed 42.58% dichloride (w/w)

Data obtained are reported in Table III below.

Five ml of the above formulation provides each animal with 50 mg STP, 25 mg pyridine, 2.5 mg silicone defoamer, 1074.5 mg (cation) of the toxicant 1,1'-dimethyl-4,4'-bipyridinium dichloride, and 337.5 mg of surfactant monylphenol condensed with 20 moles of ethylene oxide.

TABLE III

Determination of emesis in beagle dogs dosed with 5 ml of a 21.49% aqueous solution of 1,1'-dimethyl-4,4'-bipyridinium dichloride containing 1% of sodium tripolyphosphate and 0.5% pyridine
Summary of Experimental Results

| Dog No. and Sex | Body Wt. (kg) | Dose Solution ml/dog | Toxicant mg/kg* | Onset of Emesis (minutes) |
|---|---|---|---|---|
| 11-M | 8.0 | 5 | 134.3 | 15 |
| 12-M | 10.0 | 5 | 107.5 | 18 |
| 13-F | 7.7 | 5 | 139.6 | 18 |
| 14-F | 7.0 | 5 | 153.5 | 11 |
| Average | 8.2 |  | 133.7 | 15.5 |

*1,1'-Dimethyl-4,4'-bipyridinium cation mg/kg of animal body weight.

From the above results, it can be seen that emesis occurred in all animals an average of 15.5 minutes after dosing.

EXAMPLE 4

Determination of emesis in beagle dogs dosed with 5 ml of a 10.54% aqueous solution of 1,1'-dimethyl-4,4'-bipyridinium dichloride containing 2% of sodium tripolyphosphate and 0.50% of pyridine The procedure of Example 2 was repeated using three beagle dogs eight to 16 months of age and weighing 9.6 kg for the male and 6.3 to 7.4 kg for the females.

The toxicant formulation administered to the animals had the following composition:

| Test Solution Ingredient | % of W/V |
|---|---|
| 1,1'-Dimethyl-4,4'-bipyridinium dichloride* | 10.54 (cation) |
| Nonylphenol condensed with 20 moles of ethylene oxide | 4.50 |
| Pyridine (stench) | 0.50 |
| Silicone defoamer | 0.05 |
| Sodium tripolyphosphate | 2.00 |
| Water, qs to 100% |  |

*40% technical aqueous solution.

Five ml of the above formulation provides each animal with 100 mg STP, 25 mg pyridine, 2.5 mg silicone defoamer, 527.0 mg (cation) of the toxicant 1,1'-dimethyl-4,4'-bipyridinium dichloride and 225.0 of the surfactant nonylphenol condensed with 20 moles of ethylene oxide.

Data obtained are reported in Table IV below.

TABLE IV

Determination of emesis in beagle dogs dosed with 5 ml of a 10.54% aqueous solution 1,1'-dimethyl-4,4'-bipyridinium dichloride containing 2% of sodium tripolyphosphate and 0.5% pyridine
Summary of Experimental Results

| Dog No. and Sex | Body Wt. (kg) | Dose Solution ml/dog | Toxicant mg/kg* | Onset of Emesis (minutes) |
|---|---|---|---|---|
| 15-M | 9.6 | 5 | 54.9 | 2.0 |
| 16-F | 6.3 | 5 | 83.7 | 23.0 |
| 17-F | 7.4 | 5 | 71.2 | 14.0 |
| Average | 7.8 |  | 69.9 | 13.0 |

*1,1'-Dimethyl-4,4'-bipyridinium cation mg/kg of animal body weight.

From the above results, it can be seen that emesis occurred in all animals an average of 13.0 minutes after dosing.

EXAMPLE 5

Comparative determination of emesis in beagle dogs dosed with 5 ml of (i) an 17.72% aqueous solution of 1,1'-dimethyl-4,4'-bipyridinium dichloride containing 2% of sodium tripolyphosphate, no pyridine or (ii) a similar 16.71% toxicant solution, but containing no sodium tripolyphosphate and no pyridine The procedure of Example 2 was repeated using beagle dogs 12 to 24 months of age and weighing 8.2 to 12.7 kg for the males and 7.2 to 8.5 kg for the females.

The toxicant formulations administered to the animals had the following compositions:

| Test Solution Ingredient | % of W/V |
|---|---|
| Formulation (i) | |
| 1,1'-Dimethyl-4,4'-bipyridinium dichloride | 17.72 (cation) |
| Nonylphenol condensed with 9 moles of ethylene oxide | 4.89 |
| Sodium tripolyphosphate | 2.18 |
| Water, qs to 100% | |
| Formulation (ii) | |
| 1,1'-Dimethyl-4,4'-bipyridinium dichloride* | 16.71 (cation) |
| Nonylphenol condensed with 9 moles of ethylene oxide | 4.80 |
| Water, qs to 100% | |

*40% technical aqueous solution assayed 42.58% dichloride (w/w)

Five ml of the (i) formulation provides each animal with 109 mg STP, no pyridine, no silicone defoamer, 886 mg (cation) of the toxicant 1,1'-dimethyl-4,4'-bipyridinium dichloride and 244.5 mg of the surfactant nonylphenol condensed with 9 moles of ethylene oxide.

Five ml of the (ii) formulation provides each animal with 835.5 mg (cation) of the toxicant 1,1'-dimethyl-4,4'-bipyridinium dichloride and 240 mg of the surfactant nonylphenol condensed with 9 moles of ethylene oxide but no STP, no pyridine, and no silicone defoamer.

Data obtained are reported in Table V below.

TABLE V

Comparative determination of emesis in beagle dogs dosed with 5 ml of (i) an 17.72% aqueous solution of 1,1'-dimethyl-4,4'-bipyridinium dichloride containing 2% of sodium tripolyphosphate, and (ii) a similiar 16.71% toxicant solution, but containing no sodium tripolyphosphate and no pyridine
Summary of Experimental Results

| Dog No. and Sex | Body Wt. (kg) | Dose Solution ml/dog | Dose Toxicant mg/kg* | Onset of Emesis (minutes) |
|---|---|---|---|---|
| Formulation (i) | | | | |
| 18-M | 8.2 | 5 | 108.1 | 24.0 |
| 19-M | 12.2 | 5 | 72.6 | 10.0 |
| 20-F | 8.8 | 5 | 100.7 | 14.0 |
| Average | 9.7 | | 93.8 | 16.0 |
| Formulation (ii) | | | | |
| 21-M | 12.7 | 5 | 65.8 | NE |
| 22-M | 9.5 | 5 | 88.0 | 23.0 |
| 23-F | 8.5 | 5 | 98.3 | 68.0 |
| 24-F | 7.3 | 5 | 114.5 | 373.0 |
| Average | 9.5 | | 91.7 | 120.5 |

*1,1'-Dimethyl-4,4'-bipyridinium cation mg/kg of animal body weight
NE = no emesis From the above data, it can be seen that emesis occurred in all animals receiving the (i) formulation containing 17.72% of 1,1'-dimethyl-4,4'-bipyridinium dichloride and 2.18% sodium tripolyphosphate; whereas, emesis did not occur or occurred an average of 120.5 minutes after dosing with the (ii) formulation containing 16.71% of 1,1'-dimethyl-4,4'-bipyridinium dichloride but no sodium tripolyphosphate.

EXAMPLE 6

Determination of emesis in beagle dogs dosed with 1 ml of an 17.72% aqueous solution of 1,1'-dimethyl-4,4'-bipyridinium dichloride containing 2% sodium tripolyphosphate and no pyridine The procedure of Example 2 was repeated using beagle dogs eight to 16 months of age and weighing 7.3 to 9.5 kg for males and 7.8 kg for females.

The toxicant formulation administered to the animals had the following composition.

| Test Solution Ingredient | % W/V |
|---|---|
| 1,1'-Dimethyl-4,4'-bipyridinium dichloride* | 17.72 (cation) |
| Nonylphenol condensed with 20 moles of ethylene oxide | 4.89 |
| Sodium tripolyphosphate | 2.18 |
| Water, qs to 100% | |

*40% technical aqueous solution assayed 42.58% dichloride (w/w)

One ml of the above formulation provides each animal with 21.8 mg STP, no pyridine, no silicone defoamer, 177.2 mg of the toxicant 1,1'-dimethyl-4,4'-bipyridinium dichloride and 48.90 mg of the surfactant nonylphenol condensed with 20 moles of ethylene oxide.

Data obtained are reported below.

TABLE VI

Determination of emesis in beagle dogs dosed with 1 ml of an 17.72% aqueous solution of 1,1'-dimethyl-4,4'-bipyridinium dichloride containing 2% sodium tripolyphosphate and no pyridine
Summary of Experimental Results

| Dog No. and Sex | Body Wt. (kg) | Dose Solution ml/dog | Dose Toxicant mg/kg* | Onset of Emesis (minutes) |
|---|---|---|---|---|
| 25-M | 9.5 | 1 | 18.7 | 22.0 |
| 26-M | 7.3 | 1 | 24.3 | NE |
| 27-F | 7.8 | 1 | 22.7 | 25.0 |
| 28-F | 7.8 | 1 | 22.7 | 29.0 |
| Average | 8.1 | | 22.1 | 25.3 |

*1,1'-Dimethyl-4,4'-bipyridinium cation mg/kg of animal body weight.
NE = no emesis.

From the above data, it can be seen that, in dogs receiving only 1 ml of toxicant solution containing 17.72% of 1,1'-dimethyl-4,4'-bipyridinium dichloride and 2% sodium tripolyphosphate, emesis occurred an average of 25.3 minutes after dosing or not at all.

EXAMPLE 7

Determination of emesis in beagle dogs dosed with 2.5 ml of a 17.72% 1,1'-dimethyl-4,4'-bipyridinium dichloride aqueous solution containing 1.0% of sodium tripolyphosphate and 0.5% pyridine Following the procedure of Example 2 above, eight to 16 month old beagle dogs weighing 8.2 to 10 kg for males and 6.8 to 8.4 kg for females were dosed with 2.5 ml of an aqueous solution containing 20% W/V of 1,1'-dimethyl-4,4'-bipyridinium dichloride and 1% W/V of sodium tripolyphosphate.

The toxicant formulation administered to the animals had the following composition:

| Test Solution Ingredient | % W/V |
|---|---|
| 1,1'-Dimethyl-4,4'-bipyridinium dichloride* | 17.72 (cation) |
| Nonylphenol condensed with 20 moles of ethylene oxide | 6.75 |
| Pyridine (stench) | 0.50 |
| Silicone defoamer | 0.05 |
| Sodium tripolyphosphate | 1.00 |
| Water, qs to 100% | |

*40% technical aqueous solution assayed 42.58 dichloride (w/w)

2.5 ml of the above formulation provides each animal with 25 mg STP, 12.5 mg pyridine, 1.25 mg silicone defoamer, 443 mg (cation) of the toxicant 1,1'-dimethyl-4,4'-bipyridinium dichloride and 168.75 mg of the surfactant nonylphenol condensed with 20 moles of ethylene oxide.

Data obtained are reported in Table VII below.

TABLE VII

Determination of emesis in beagle dogs dosed with 2.5 ml of a 17.72% aqueous solution of 1,1'-dimethyl-4,4'-bipyridinium dichloride containing 1.0% of sodium tripolyphosphate and 0.5% pyridine
Summary of Experimental results

| Dog No. and Sex | Body Wt. (kg) | Dose Solution ml/dog | Dose Toxicant mg/kg | Onset of Emesis (minutes) |
|---|---|---|---|---|
| 29-M | 9.2 | 2.5 | 48.2 | 28.0 |
| 30-M | 8.2 | 2.5 | 54.0 | 27.0 |
| 31-M | 9.0 | 2.5 | 49.2 | 41.0 |
| 32-M | 8.2 | 2.5 | 54.0 | 16.0 |
| 33-M | 10.0 | 2.5 | 44.3 | 30.0 |

TABLE VII-continued

Determination of emesis in beagle dogs dosed with 2.5 ml of a 17.72% aqueous solution of 1,1'-dimethyl-4,4'-bipyridinium dichloride containing 1.0% of sodium tripolyphosphate and 0.5% pyridine
Summary of Experimental results

| Dog No. and Sex | Body Wt. (kg) | Dose Solution ml/dog | Dose Toxicant mg/kg | Onset of Emesis (minutes) |
|---|---|---|---|---|
| 34-F | 7.0 | 2.5 | 63.3 | 17.0 |
| 35-F | 6.8 | 2.5 | 65.2 | 66.0 |
| 36-F | 8.3 | 2.5 | 53.4 | 10.0 |
| 37-F | 7.8 | 2.5 | 56.8 | 7.0 |
| 38-F | 8.4 | 2.5 | 52.7 | 9.0 |
| Average | 8.3 | | 54.1 | 25.1 |

*1,1'-Dimethyl-4,4'-bipyridinium cation mg/kg of animal body weight.

From the above data, it can be seen that, in dogs receiving 2.5 ml of toxicant solution containing 17.72% of 1,1'-dimethyl-4,4'-bipyridinium dichloride and 1.0% of sodium tripolyphosphate and 0.5% pyridine, emesis occurred an average of 25.1 minutes after dosing.

EXAMPLE 8

Determination of emesis in beagle dogs receiving 5 ml of a solution containing 18.07% W/V of 1,1'-dimethyl-4,4'-bipyridinium dichloride, 1.0% sodium tripolyphosphate and no pyridine Following the procedure of Example 2, eight to 16 month old beagle dogs weighing 10.6 kg to 10.8 kg for males and 6.5 kg to 10.5 kg for females are administered 5 ml of an aqueous solution containing 18.07% W/V of 1,1'-dimethyl-4,4'-bipyridinium dichloride, 1% W/V of sodium tripolyphosphate, no pyridine, and no silicone defoamer. The solution administered to said dogs had the following composition.

| Test Solution | |
|---|---|
| Ingredient | % W/V |
| 1,1'-Dimethyl-4,4'-bipyridinium dichloride* | 18.07 (cation) |
| Sodium tripolyphosphate | 1.0 |
| Water, qs to 100% | |

*40% technical aqueous solution assayed 42.58% dichloride (w/w)

Five ml of the above formulation provided each dog with 50 mg of sodium tripolyphosphate, no pyridine, no silicone defoamer, 900.4 mg of the toxicant 1,1'-dimethyl-4,4'-bipyridinium dichloride, and no surfactant.

Data obtained are reported in Table VIII below.

TABLE VIII

Determination of emesis in beagle dogs receiving 5 ml of a solution containing 18.07% W/V of 1,1'-dimethyl-4,4'-bipyridinium dichloride, 1.0% W/V of sodium tripolyphosphate and no pyridine
Summary of Experimental Results

| Dog No. and Sex | Body Wt. (kg) | Dose Solution ml/dog | Dose Toxicant mg/kg* | Onset of Emesis (minutes) |
|---|---|---|---|---|
| 39-M | 10.6 | 5 | 85.2 | 45.0 |
| 40-M | 10.8 | 5 | 83.7 | 8.0 |
| 41-F | 10.5 | 5 | 86.1 | 36.0 |
| 42-F | 6.5 | 5 | 139.0 | 17.0 |
| Average | 9.6 | | 98.5 | 26.5 |

*1,1'-Dimethyl-4,4'-bipyridinium cation mg/kg of animal body weight.

From the above data, it can be seen that in dogs receiving 5 ml of toxicant solution containing 18.07% of 1,1'-dimethyl-4,4'-bipyridinium dichloride, 1.0% of sodium tripolyphosphate, and no pyridine emesis occurred an average of 26.5 minutes after dosing.

EXAMPLE 9

Determination of emesis in beagle dogs dosed with 5 ml of a 9.07% aqueous solution of 1,1'-dimethyl-4,4'-bipyridinium dichloride containing 0.5% sodium tripolyphosphate and 0.25% pyridine Following the procedure of Example 2, eight to 16 month old beagle dogs weighing 7.4 to 7.6 kg for males and 6.8 to 7.3 kg for females were administered 5 ml of an aqueous solution containing 9.07 W/V (cation) of 1,1'-dimethyl-4,4'-bipyridinium dichloride, 0.50% W/V of sodium tripolyphosphate, 0.25% W/V of sodium tripolyphosphate, 3.375% W/V of nonylphenol condensed with 20 moles of ethylene oxide and 0.025% W/V of silicone defoamer. The solution administered to said dogs had the following composition:

| Test Solution | |
|---|---|
| Ingredient | % W/V |
| 1,1'-Dimethyl-4,4'-bipyridinium dichloride* | 9.07 (cation) |
| Nonylphenol condensed with 20 moles of ethylene oxide | 3.375 |
| Pyridine (stench) | 0.25 |
| Silicone defoamer | 0.025 |
| Sodium tripolyphosphate | 0.50 |
| Water - qs to 100% | |

*40% technical aqueous solution assayed 42.58% dichloride (w/w)

Five ml of the above solution provides the animal with 25 mg STP, 12.5 mg pyridine, 1.25 mg silicone defoamer, 453.5 mg (cation) of the toxicant 1,1'-dimethyl-4,4'-bipyridinium dichloride and 168.75 mg of the surfactant nonylphenol condensed with 20 moles of ethylene oxide.

TABLE IX

Determination of emesis in beagle dogs dosed with 5 ml of a 9.07% aqueous solution of 1,1'-dimethyl-4,4'-bipyridinium dichloride containing 0.5% sodium tripolyphosphate and 0.25% pyridine
Summary of Experimental Results

| Dog No. and sex | Body wt. (kg) | Dose Solution ml/dog | Dose Toxicant mg/kg* | Onset of Emesis (minutes) |
|---|---|---|---|---|
| 43-M | 7.6 | 5 | 59.7 | 47 |
| 44-M | 7.4 | 5 | 61.3 | 48 |
| 45-F | 7.3 | 5 | 62.1 | 24 |
| 46-F | 6.8 | 5 | 66.7 | 33 |
| Average | 7.28 | | 62.5 | 38 |

*1,1'-Dimethyl-4,4'-bipyridinium cation mg/kg of animal body weight.

From the above data, it can be seen that in dogs receiving 5 ml of the toxicant solution containing 9.07% of 1,1'-dimethyl-4,4'-bipyridinium dichloride, 0.50% sodium tripolyphosphate, and 0.25% pyridine, emesis occurred an average of 38 minutes after dosing.

EXAMPLE 10

Determination of emesis in beagle dogs dosed with 1.4 to 2.2 ml of a 18.96% aqueous solution of 1,1'-dimethyl-4,4'-bipyridinium dichloride containing 1.5% sodium tripolyphosphate and 0.5% pyridine The procedure of Example 2 was repeated using 10 beagle dogs eight to 16 months of age and weighing 7.7 to 8.7 kg for males and 5.5 to 7.5 for females.

The toxicant formulation administered to the animals had the following composition:

| Ingredient | Test Solution % W/V |
|---|---|
| 1,1'-Dimethyl-4,4'-bipyridinium dichloride* | 18.96 (cation) |
| Nonylphenol condensed with 20 moles of ethylene oxide | 6.75 |
| Pyridine (stench) | 0.50 |
| Silicone (defoamer) | 0.05 |
| Sodium tripolyphosphate | 1.50 |
| Water - qs to 100% | |

*40% technical aqueous solution assayed 42.58% dichloride (w/w)

In these tests, the animals were dosed with 1.8 ml of the test solution which provides the animal with 27 mg of STP, 9 mg of pyridine, 0.9 mg of silicone defoamer, 341.3 mg (cation) of the toxicant 1,1'-dimethyl-4,4'-bipyridinium dichloride and 121.50 mg of the surfactant nonylphenol condensed with 20 moles of ethylene oxide.

TABLE X

Determination of emesis in beagle dogs dosed with 1.8 ml of a 18.96% aqueous solution of 1,1'-dimethyl-4,4'-bipyridinium dichloride containing 1.5% sodium tripolyphosphate and 0.5% pyridine
Summary of Experimental Results

| Dog No and sex | Body wt (kg) | Dose Solution ml/dog | Dose Toxicant mg/kg* | Onset of Emesis (minutes) |
|---|---|---|---|---|
| 47-M | 8.7 | 2.2 | 47.9 | 25.0 |
| 48-M | 8.4 | 2.1 | 47.4 | 23.0 |
| 49-M | 8.7 | 2.2 | 47.9 | 39.0 |
| 50-M | 8.3 | 2.1 | 48.0 | 46.0 |
| 51-M | 7.7 | 1.9 | 46.8 | 29.0 |
| 52-F | 7.5 | 1.9 | 48.0 | 99.0 |
| 53-F | 6.5 | 1.6 | 46.7 | 22.0 |
| 54-F | 6.4 | 1.6 | 47.4 | 20.0 |
| 55-F | 5.7 | 1.4 | 46.6 | 64.0 |
| 56-F | 5.5 | 1.4 | 48.3 | 32.0 |
| Average | 7.4 | 1.8 | 47.5 | 38.2 |

EXAMPLE 11

Determination of emesis in beagle dogs dosed with 5 ml of a 18.96% aqueous solution of 1,1'-dimethyl-4,4'-bipyridinium dichloride containing 1.0% sodium tripolyphosphate and 1.0% pyridine Following the procedure of Example 2, eight to 16 month old beagle dogs weighing 7.2 to 8.2 kg for males and 7.7 to 8.3 kg for females were acclimatized to laboratory conditions for at least two weeks prior to testing. Thereafter, each dog was dosed, as described in Example 1, with 5 ml of an aqueous test solution described below:

| Ingredient | Test Solution % W/V |
|---|---|
| 1,1'-Dimethyl-4,4'-bipyridinium dichloride* | 18.96 (cation) |
| Nonylphenol condensed with 20 moles of ethylene oxide | 6.75 |
| Pyridine (stench) | 1.00 |
| Silicone defoamer | 0.05 |
| Sodium tripolyphosphate | 1.00 |
| HCl, adjust pH to 6.8 | |
| Water - qs to 100% | |

*40% technical aqueous solution assayed 42.58% dichloride (w/w)

Five ml of the above solution provides each animal with 50 mg STP, 50 mg pyridine, 2.5 mg silicone defoamer, 948 mg (cation) of the toxicant 1,1'-dimethyl-4,4'-bipyridinium dichloride and 337.5 mg of the surfactant nonylphenol condensed with 20 moles of ethylene oxide.

TABLE XI

Determination of emesis in beagle dogs with 5 ml of a 18.96% aqueous solution of 1,1'-dimethyl-4,4'-bipyridinium dichloride containing 1.0% sodium tripolyphosphate and 1.0% pyridine.
Summary of Experimental Results

| Dog No. and Sex | Body Wt. (kg) | Dose Solution ml/dog | Dose Toxicant mg/kg* | Onset of Emesis (Minutes) |
|---|---|---|---|---|
| 57-M | 7.2 | 5 | 131.7 | 16.0 |
| 58-M | 8.2 | 5 | 115.6 | 29.0 |
| 59-F | 7.7 | 5 | 123.1 | 10.0 |
| 60-F | 8.3 | 5 | 114.2 | 8.0 |
| Average | 7.85 | | 121.2 | 15.75 |

*1,1'-Dimethyl-4,4'-bipyridinium dichloride mg/kg of animal body weight.

From the above data, it can be seen that emesis occurred in all dogs an average of 15.75 minutes after dosing.

EXAMPLE 12

Comparison of data obtained in Examples 1–11

The compositions evaluated in Examples 1–11 above, and the results obtained are compared in Tables XII–XV below. From the results, it can be seen that the addition of from 21.8 mg of 50 mg (1% to 2% W/V) of STP to an aqueous solution containing a nominal 20% W/V of the toxicant 1,1'-dimethyl-4,4'-bipyridinium dichloride unexpectedly causes emesis in dogs in about 1/5 of the time taken by dogs ingesting an aqueous solution containing a nominal 20% W/V of the toxicant alone.

It can also be seen that the addition of 12.5 mg of pyridine plus 25 mg (1% W/V) of STP to an aqueous 18% W/V solution of the above-said toxicant did not further reduce the time to onset of emesis in dogs ingesting the above-said STP-toxicant solution; whereas, it was surprisingly found that the addition of 25 to 50 mg (0.5% to 1.0% W/V) of pyridine added to a 10% to 20% W/V aqueous solution of the above-said toxicant containing 50 to 100 mg (1% to 2% W/V) of STP, produced an additional 44% reduction in time to onset of emesis over dogs ingesting either of the above-mentioned STP-toxicant or STP-toxicant-pyridine solutions.

The unexpected improvement in reduced time to emesis achieved with the latter composition which contains 50–100 mg (1% to 2% W/V) STP plus 25 to 50 mg (0.50%–1.0% W/V) pyridine plus 10% to 20% of 1,1'-dimethyl-4,4'-bipyridinium dichloride, is graphically illustrated in FIG. 1 below.

TABLE XII

Average time to onset of emesis in beagle dogs receiving toxicant, toxicant + STP or toxicant + STP + pyridine
Summary of Experimental Results

| STP mg/dog | Pyridine mg/dog | Silicone Defoamer mg/dog | Toxicant mg/dog | Toxicant mg/ml | Toxicant ml/dog | Avg. Dog Body wt. (kg) | Surfactant mg/dog | Onset of Emesis (minutes) |
|---|---|---|---|---|---|---|---|---|
| 0 | 0 | 0 | 886.0 | 177.2 | 5.0 | 9.5 | 240.0 | 120.5 |
| 21.8 | 0 | 0 | 177.2 | 177.2 | 1.0 | 8.1 | 48.90 | 25.3 |
| 25.0 | 12.5 | 1.25 | 453.5 | 90.7 | 5.0 | 6.6 | 168.75 | 38.0 |
| 25.0 | 12.5 | 1.25 | 443.0 | 177.2 | 2.5 | 8.3 | 168.75 | 25.1 |
| 27.0 | 9.0 | 0.9 | 341.3 | 189.6 | 1.8 | 7.4 | 121.50 | 38.2 |
| 50.0 | 0 | 0 | 0 | 0 | 5.0 | 10.3 | 0 | NE |
| 50.0 | 0 | 0 | 900.4 | 180.7 | 5.0 | 9.6 | 0 | 26.5 |
| 50.0 | 25.0 | 2.5 | 1074.5 | 214.9 | 5.0 | 8.2 | 337.5 | 15.5 |
| 50.0 | 25.0 | 2.5 | 1002.5 | 200.5 | 5.0 | 7.5 | 337.5 | 14.2 |
| 50.0 | 50.0 | 2.5 | 948.0 | 189.6 | 5.0 | 7.9 | 337.5 | 15.8 |
| 100.0 | 25.0 | 2.5 | 527.0 | 105.4 | 5.0 | 7.8 | 225.0 | 13.0 |
| 109.0 | 0 | 0 | 835.5 | 167.1 | 5.0 | 9.7 | 244.5 | 16.0 |

NE = No Emesis

TABLE XIII

Average time to onset of emesis in beagle dogs receiving 5 ml of a 10% toxicant solution containing approximately 500 mg of toxicant, alone or in combination with STP or STP + pyridine
Summary of Experimental Results

| STP mg/ml | STP mg/dog | Pyridine mg/ml | Pyridine mg/dog | Toxicant mg/ml | Toxicant mg/dog | Onset of Emesis (minutes) |
|---|---|---|---|---|---|---|
| 10.0 | 50.0 | 0 | 0 | 0 | 0 | NE |
| 5.0 | 25.0 | 2.5 | 90.7 | 453.5 | 500.0 | 38.0 |
| 20.0 | 100.0 | 5.0 | 105.4 | 527.0 | 615.0 | 13.0 |

NE = No Emesis

TABLE XIV

Average time to onset of emesis in beagle dogs receiving 5 ml of a 20% toxicant solution containing approximately 1000 mg of toxicant, alone or in combination with STP or STP + pyridine
Summary of Experimental Results

| STP mg/ml | STP mg/dog | Pyridine mg/ml | Pyridine mg/dog | Toxicant mg/ml | Toxicant mg/dog | Onset of Emesis (minutes) |
|---|---|---|---|---|---|---|
| 10.0 | 50.0 | 0 | 0 | 0 | 0 | NE |
| 0 | 0 | 0 | 0 | 177.2 | 886.0 | 120.5 |
| 10.0 | 50.0 | 0 | 0 | 180.7 | 900.4 | 26.5 |
| 10.0 | 50.0 | 5.0 | 25.0 | 214.9 | 1074.5 | 15.5 |
| 10.0 | 50.0 | 5.0 | 25.0 | 200.5 | 1002.5 | 14.2 |
| 10.0 | 50.0 | 10.0 | 50.0 | 189.6 | 948.0 | 15.8 |
| 20.0 | 109.0 | 0 | 0 | 167.1 | 835.5 | 16.0 |

NE = No Emesis

TABLE XV

Average time to onset of emesis in beagle dogs receiving toxicant, toxicant + STP or toxicant + STP + pyridine
Summary of Experimental Results

| STP mg/dog | STP body wt. mg/kg | Pyridine mg/dog | Pyridine body wt. mg/kg | Toxicant mg/ml | Toxicant ml/dog | Avg. Dog body wt. (kg) | Onset of Emesis (minutes) |
|---|---|---|---|---|---|---|---|
| 0 | 0 | 0 | 0 | 177.2 | 5.0 | 9.5 | 120.5 |
| 21.8 | 2.69 | 0 | 0 | 177.2 | 1.0 | 8.1 | 25.3 |
| 27.0 | 3.65 | 9.0 | 1.22 | 189.6 | 1.8 | 7.4 | 38.2 |
| 25.0 | 3.79 | 12.5 | 1.89 | 90.7 | 5.0 | 6.6 | 38.0 |
| 25.0 | 3.01 | 12.5 | 1.51 | 177.2 | 2.5 | 8.3 | 25.1 |
| 50.0 | 4.85 | 0 | 0 | 0 | 5.0 | 10.3 | NE |
| 50.0 | 5.21 | 0 | 0 | 180.7 | 5.0 | 9.6 | 26.5 |
| 50.0 | 6.10 | 25.0 | 3.05 | 214.9 | 5.0 | 8.2 | 15.5 |
| 50.0 | 6.67 | 25.0 | 3.33 | 200.5 | 5.0 | 7.5 | 14.2 |
| 50.0 | 6.37 | 50.0 | 6.37 | 189.6 | 5.0 | 7.9 | 15.8 |
| 100.0 | 12.82 | 25.0 | 3.21 | 105.4 | 5.0 | 7.8 | 13.0 |
| 109.0 | 11.42 | 0 | 0 | 167.1 | 5.0 | 9.7 | 16.0 |

NE = No Emesis

What is claimed is:

1. A concentrated emetic herbicidal composition comprising an aqueous solution of about 100 to 250 mg/ml of the cation of 1,1'-dimethyl-4,4'-bipyridinium dichloride; about 10 to 20 mg/ml of the peripherally-acting emetic sodium tripolyphosphate; about 5 to 10 mg/ml of the malodorous synergist pyridine for the peripheral emetic; and about 45 to 67.5 mg/ml of a nonionic surfactant.

2. A composition according to claim 1 which contains about 0.5 to 0.75 mg/ml of silicone defoamer and about 45 to 67.5 mg/ml of the surfactant polyoxyethylene ethers of octyl and nonylphenols.

3. A composition according to claim 2 which contains about 200 mg/ml of the cation of 1,1'-dimethyl-4,4'-bipyridinium dichloride; 10 mg/ml of sodium tripolyphosphate; 5 mg/ml of pyridine; 0.5 mg/ml of silicone defoamer and 67.5 mg/ml of nonylphenol condensed with 20 moles of ethylene oxide.

4. A method of rendering emetic an aqueous herbicidal composition containing about 100 to 250 mg/ml of the cation of 1,1'-dimethyl-4-4'-bipyridinium dichloride, comprising admixing therewith about 10 to 20 mg/ml of the peripherally-acting emetic sodium tripolyphosphate; about 5 to 10 mg/ml the malodorous synergist pyridine; and about 45 to 67.5 mg/ml of a nonionic surfactant.

5. A method according to claim 4 wherein the surfactant is polyoxyethylene ethers of octyl and nonylphenols, and additionally admixing about 0.5 to 0.75 mg/ml of a silicone defoamer.

6. A method according to claim 5 wherein the surfactant is nonylphenol condensed with 20 moles of ethylene oxide.

* * * * *